United States Patent [19]

Nohr et al.

[11] Patent Number: 5,643,701

[45] Date of Patent: Jul. 1, 1997

[54] ELECTROPHOTGRAPHIC PROCESS UTILIZING MUTABLE COLORED COMPOSITION

[75] Inventors: Ronald Sinclair Nohr, Roswell; John Gavin MacDonald, Decatur, both of Ga.; Vincent Daniel McGinniss, Sunbury; Robert Samuel Whitmore, Jr., Columbus, both of Ohio

[73] Assignee: Kimberly-Clark Corporation, Neenah, Wis.

[21] Appl. No.: 457,025

[22] Filed: Jun. 1, 1995

Related U.S. Application Data

[63] Continuation of Ser. No. 393,089, Feb. 22, 1995, which is a continuation of Ser. No. 103,503, Aug. 5, 1993, abandoned.

[51] Int. Cl.$^6$ .............. G03G 13/01; G03G 9/00; G03G 13/14
[52] U.S. Cl. .............. 430/47; 430/106; 430/109; 430/126
[58] Field of Search .............. 430/106, 109, 430/126

[56] References Cited

U.S. PATENT DOCUMENTS

| | | |
|---|---|---|
| Re. 28,225 | 11/1974 | Heseltine et al. . |
| Re. 28,789 | 4/1976 | Chang . |
| 575,228 | 1/1897 | von Gallois . |
| 582,853 | 5/1897 | Feer . |
| 1,013,544 | 1/1912 | Fuerth . |
| 1,325,971 | 12/1919 | Akashi . |
| 1,364,406 | 1/1921 | Olsen . |
| 1,436,856 | 11/1922 | Brenizer et al. . |
| 1,744,149 | 1/1930 | Staechlin . |
| 1,803,906 | 5/1931 | Krieger et al. . |
| 1,876,880 | 9/1932 | Drapal . |
| 1,880,572 | 10/1932 | Wendt et al. . |
| 1,880,573 | 10/1932 | Wendt et al. . |
| 1,916,350 | 7/1933 | Wendt et al. . |
| 1,916,779 | 7/1933 | Wendt et al. . |
| 1,955,898 | 4/1934 | Wendt et al. . |
| 1,962,111 | 6/1934 | Bamberger . |
| 2,049,005 | 7/1936 | Gaspar . |
| 2,054,390 | 9/1936 | Rust et al. . |
| 2,062,304 | 12/1936 | Gaspar . |
| 2,097,119 | 10/1937 | Eggert . |
| 2,106,539 | 2/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,159,280 | 5/1939 | Mannes et al. . |
| 2,171,976 | 9/1939 | Erickson . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |
| 2,242,431 | 12/1941 | Hara et al. . |
| 2,268,324 | 12/1941 | Polgar . |

(List continued on next page.)

FOREIGN PATENT DOCUMENTS

| | | |
|---|---|---|
| 103085 | 4/1937 | Australia . |
| 12624/88 | 9/1988 | Australia . |
| 620075 | 5/1962 | Belgium . |
| 637169 | 3/1964 | Belgium . |
| 413257 | of 0000 | Canada . |
| 275245 | 10/1928 | Canada . |
| 458808 | 12/1936 | Canada . |
| 460268 | 10/1949 | Canada . |
| 461082 | 11/1949 | Canada . |
| 463022 | 2/1950 | Canada . |
| 463021 | 2/1950 | Canada . |
| 465495 | 5/1950 | Canada . |
| 465496 | 5/1950 | Canada . |

(List continued on next page.)

OTHER PUBLICATIONS

Abstract for WO 9500343—A1, *Textiles: Paper: Cellulose*, p. 7, (1995).

Brennan et al., "Stereoelectronic effects in ring closure reactions: the 2'-hydroxychalcone—flavanone equilibrium, and related systems," *Canadian J. Chem.*, 68:17–80–1785 (1990).

Sakai et al., "A Novel and Practical Synthetiuc Method of 3(2H)–Furanone Derivatives," *J. Heterocyclie Chem.*, 23:1199–1201 (1986).

Kano et al., "Three–Component Complexes of Cyclodextrins. Exciplex Formation in Cyclodextrin Cavity," *J. Inclusion Phenomena 2*, pp. 737–746 (1984).

Susuki et al., "Spectroscopic Investigation of Cyclodextrin Monomers, Derivatives, Polymers and Azo Dyes," *J. Inclusion Phenomena 2*, pp. 715–724 (1984).

Semple et al., "Synthesis of Functionalized Tetrahydrofurans," *Tetrahedron Letters*, 81:4561–4564 (1980).

(List continued on next page.)

*Primary Examiner*—Glenn A. Caldarola
*Assistant Examiner*—J. Pasterczyk
*Attorney, Agent, or Firm*—Jones & Askew

[57] ABSTRACT

An electrophotographic process wherein an image is formed with toner comprising a mutable colorant and an ultraviolet radiation transorber so that an image formed by the electrophotographic process can be altered in color or erased. The electrophotographic process comprises the steps of creating an image on a photoreceptor surface, applying a toner on the photoreceptor surface to form a toner image which replicates the image, transferring the toner image to a substrate, and fixing the toner image to the substrate. The toner comprises a mutable colorant, an ultraviolet radiation transorber, and a carrier comprising a polymer. The ultraviolet radiation transorber is adapted, upon exposure to ultraviolet radiation, to interact with the mutable colorant to irreversibly mutate the mutable colorant from an initial absorption maximum to a new absorption maximum different from the initial absorption maximum. The electrophotographic process may further comprise exposing the toner image on the substrate to ultraviolet radiation at a dosage level sufficient to irreversibly mutate the colorant and change the color of the toner image or render the image colorless. The substrate can then be reused to form a second toner image thereon.

23 Claims, No Drawings

U.S. PATENT DOCUMENTS

| | | |
|---|---|---|
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,601,669 | 6/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,728,784 | 12/1955 | Tholstrup et al. . |
| 2,732,301 | 1/1956 | Robertson et al. ............................ 95/7 |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,834,773 | 4/1958 | Scalera et al. . |
| 2,897,187 | 7/1959 | Koch . |
| 2,936,241 | 5/1960 | Sharp et al. . |
| 2,940,853 | 6/1960 | Sagura et al. ................................ 96/91 |
| 2,992,198 | 7/1961 | Funahashi . |
| 3,030,208 | 4/1962 | Schellenberg et al. . |
| 3,071,815 | 1/1963 | MacKinnon . |
| 3,104,973 | 9/1963 | Sprague et al. . |
| 3,114,634 | 12/1963 | Brown et al. . |
| 3,121,632 | 2/1964 | Sprague et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,242,215 | 3/1966 | Heitmiller . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,359,109 | 12/1967 | Harder et al. . |
| 3,361,827 | 1/1968 | Biletch . |
| 3,385,700 | 5/1968 | Willems et al. . |
| 3,397,984 | 8/1968 | Williams et al. . |
| 3,418,118 | 12/1968 | Thommes et al. . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,547,646 | 12/1970 | Hori et al. . |
| 3,563,931 | 2/1971 | Horiguchi . |
| 3,574,624 | 4/1971 | Reynolds et al. . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |
| 3,676,690 | 7/1972 | McMillin et al. . |
| 3,678,044 | 7/1972 | Adams . |
| 3,695,879 | 10/1972 | Laming et al. . |
| 3,697,280 | 10/1972 | Strilko . |
| 3,707,371 | 12/1972 | Files . |
| 3,729,313 | 4/1973 | Smith . |
| 3,737,628 | 6/1973 | Azure . |
| 3,765,896 | 10/1973 | Fox . |
| 3,775,130 | 11/1973 | Enomoto et al. . |
| 3,788,849 | 1/1974 | Taguchi et al. . |
| 3,799,773 | 3/1974 | Watarai et al. ............................ 96/1 R |
| 3,800,439 | 4/1974 | Sokolski et al. . |
| 3,817,752 | 6/1974 | Laridon et al. . |
| 3,840,338 | 10/1974 | Zviak et al. . |
| 3,870,524 | 3/1975 | Watanabe et al. ...................... 96/115 P |
| 3,873,500 | 3/1975 | Kato et al. . |
| 3,887,450 | 6/1975 | Gilano et al. . |
| 3,895,949 | 7/1975 | Akamatsu . |
| 3,914,166 | 10/1975 | Rudolph et al. . |
| 3,915,824 | 10/1975 | McGinniss . |
| 3,919,323 | 11/1975 | Houlihan et al. . |
| 3,960,685 | 6/1976 | Sano et al. ......................... 204/159.12 |
| 3,978,132 | 8/1976 | Houlihan et al. . |
| 3,984,248 | 10/1976 | Sturmer . |
| 3,988,154 | 10/1976 | Sturmer . |
| 4,012,256 | 3/1977 | Levinos . |
| 4,043,819 | 8/1977 | Baumann . |
| 4,048,034 | 9/1977 | Martan . |
| 4,056,665 | 11/1977 | Tayler et al. . |
| 4,058,400 | 11/1977 | Crivello . |
| 4,067,892 | 1/1978 | Thorne et al. . |
| 4,073,968 | 2/1978 | Miyamoto et al. . |
| 4,079,183 | 3/1978 | Green . |
| 4,090,877 | 5/1978 | Streeper . |
| 4,100,047 | 7/1978 | McCarty . |
| 4,107,733 | 8/1978 | Schickedanz . |
| 4,110,112 | 8/1978 | Roman et al. . |
| 4,111,699 | 9/1978 | Krueger . |
| 4,114,028 | 9/1978 | Baio et al. . |
| 4,148,658 | 4/1979 | Kondoh et al. . |
| 4,162,162 | 7/1979 | Dueber . |
| 4,171,977 | 10/1979 | Hasegawa et al. ..................... 96/115 P |
| 4,179,577 | 12/1979 | Green . |
| 4,181,807 | 1/1980 | Green . |
| 4,229,172 | 10/1980 | Baumann et al. . |
| 4,232,106 | 11/1980 | Iwasaki et al. . |
| 4,239,843 | 12/1980 | Hara et al. . |
| 4,239,850 | 12/1980 | Kita et al. ................................. 430/281 |
| 4,241,155 | 12/1980 | Hara et al. . |
| 4,242,430 | 12/1980 | Hara et al. . |
| 4,245,018 | 1/1981 | Hara et al. . |
| 4,245,995 | 1/1981 | Hugl et al. . |
| 4,246,330 | 1/1981 | Hara et al. . |
| 4,248,949 | 2/1981 | Hara et al. . |
| 4,250,096 | 2/1981 | Kvita et al. . |
| 4,251,622 | 2/1981 | Kimoto et al. . |
| 4,254,195 | 3/1981 | Hara et al. . |
| 4,256,493 | 3/1981 | Yokoyama et al. . |
| 4,256,817 | 3/1981 | Hara et al. . |
| 4,258,123 | 3/1981 | Nagashima et al. .................... 430/281 |
| 4,259,432 | 3/1981 | Kondoh et al. . |
| 4,262,936 | 4/1981 | Miyamoto . |
| 4,268,605 | 5/1981 | Hara et al. . |

| | | | | | | |
|---|---|---|---|---|---|---|
| 4,268,667 | 5/1981 | Anderson . | | 4,672,041 | 6/1987 | Jain . |
| 4,269,926 | 5/1981 | Hara et al. . | | 4,698,291 | 10/1987 | Koibuchi et al. . |
| 4,270,130 | 5/1981 | Houle et al. . | | 4,701,402 | 10/1987 | Patel et al. . |
| 4,271,252 | 6/1981 | Hara et al. . | | 4,702,996 | 10/1987 | Griffing et al. . |
| 4,271,253 | 6/1981 | Hara et al. . | | 4,707,161 | 11/1987 | Thomas et al. . |
| 4,272,244 | 6/1981 | Schlick . | | 4,707,425 | 11/1987 | Sasagawa et al. . |
| 4,279,982 | 7/1981 | Iwasaki et al. . | | 4,707,430 | 11/1987 | Ozawa et al. . |
| 4,279,985 | 7/1981 | Nonogaki et al. . | | 4,720,450 | 1/1988 | Ellis . |
| 4,284,485 | 8/1981 | Berner . | | 4,721,734 | 1/1988 | Gehlhaus et al. . |
| 4,289,844 | 9/1981 | Specht et al. . | | 4,724,021 | 2/1988 | Martin et al. . |
| 4,290,870 | 9/1981 | Kondoh et al. . | | 4,724,201 | 2/1988 | Okazaki et al. . |
| 4,298,679 | 11/1981 | Shinozaki et al. ................... 430/281 | | 4,725,527 | 2/1988 | Robillard . |
| 4,300,123 | 11/1981 | McMillin et al. . | | 4,737,438 | 4/1988 | Ito et al. . |
| 4,306,014 | 12/1981 | Kunikane et al. . | | 4,740,451 | 4/1988 | Kohara . |
| 4,307,182 | 12/1981 | Dalzell et al. . | | 4,745,042 | 5/1988 | Sasago et al. . |
| 4,308,400 | 12/1981 | Felder et al. . | | 4,755,450 | 7/1988 | Sanders et al. . |
| 4,315,807 | 2/1982 | Felder et al. . | | 4,761,181 | 8/1988 | Suzuki . |
| 4,318,705 | 3/1982 | Nowak et al. . | | 4,766,050 | 8/1988 | Jerry . |
| 4,318,791 | 3/1982 | Felder et al. . | | 4,766,055 | 8/1988 | Kawabata et al. . |
| 4,335,054 | 6/1982 | Blaser et al. . | | 4,771,802 | 9/1988 | Tannenbaum . |
| 4,335,055 | 6/1982 | Blaser et al. . | | 4,772,291 | 9/1988 | Shibanai et al. . |
| 4,336,323 | 6/1982 | Winslow . | | 4,772,541 | 9/1988 | Gottschalk ....................... 430/339 |
| 4,343,891 | 8/1982 | Aasen et al. . | | 4,775,386 | 10/1988 | Reinert et al. . |
| 4,345,011 | 8/1982 | Drexhage . | | 4,786,586 | 11/1988 | Lee et al. . |
| 4,347,111 | 8/1982 | Gehlhaus et al. . | | 4,800,149 | 1/1989 | Gottschalk ....................... 430/138 |
| 4,349,617 | 9/1982 | Kawashiri et al. . | | 4,808,189 | 2/1989 | Oishi et al. . |
| 4,350,753 | 9/1982 | Shelnut et al. . | | 4,812,139 | 3/1989 | Brodmann . |
| 4,351,893 | 9/1982 | Anderson . | | 4,812,517 | 3/1989 | West . |
| 4,356,255 | 10/1982 | Tachikawa et al. . | | 4,813,970 | 3/1989 | Kirjanov et al. . |
| 4,359,524 | 11/1982 | Masuda et al. . | | 4,822,714 | 4/1989 | Sanders ....................... 430/138 |
| 4,362,806 | 12/1982 | Whitmore . | | 4,837,106 | 6/1989 | Ishikawa et al. . |
| 4,367,072 | 1/1983 | Vogtle et al. . | | 4,837,331 | 6/1989 | Yamanishi et al. . |
| 4,367,280 | 1/1983 | Kondo et al. . | | 4,838,938 | 6/1989 | Tomida et al. . |
| 4,369,283 | 1/1983 | Altschuler . | | 4,839,269 | 6/1989 | Okazaki et al. . |
| 4,370,401 | 1/1983 | Winslow et al. . | | 4,849,320 | 7/1989 | Irving et al. . |
| 4,373,020 | 2/1983 | Winslow . | | 4,853,395 | 8/1989 | Carr et al. . |
| 4,376,887 | 3/1983 | Greenaway et al. . | | 4,853,398 | 8/1989 | Carr et al. . |
| 4,390,616 | 6/1983 | Sato et al. . | | 4,857,438 | 8/1989 | Loerzer et al. . |
| 4,391,867 | 7/1983 | Derick et al. . | | 4,861,916 | 8/1989 | Kohler et al. . |
| 4,399,209 | 8/1983 | Sanders et al. ................... 430/198 | | 4,865,942 | 9/1989 | Gottschalk et al. ....................... 430/138 |
| 4,416,961 | 11/1983 | Drexhage . | | 4,874,391 | 10/1989 | Reinert . |
| 4,424,325 | 1/1984 | Tsunoda et al. . | | 4,886,774 | 12/1989 | Doi ....................... 503/226 |
| 4,425,162 | 1/1984 | Sugiyama et al. . | | 4,895,880 | 1/1990 | Gottschalk ....................... 522/31 |
| 4,425,424 | 1/1984 | Altland et al. . | | 4,900,581 | 2/1990 | Stuke et al. . |
| 4,434,035 | 2/1984 | Eichler et al. . | | 4,902,299 | 2/1990 | Anton . |
| 4,447,521 | 5/1984 | Tiers et al. . | | 4,902,725 | 2/1990 | Moore . |
| 4,450,227 | 5/1984 | Holmes et al. . | | 4,902,787 | 2/1990 | Freeman . |
| 4,460,676 | 7/1984 | Fabel . | | 4,925,770 | 5/1990 | Ichiura et al. . |
| 4,467,112 | 8/1984 | Matsuura et al. . | | 4,933,948 | 6/1990 | Herkstroeter . |
| 4,475,999 | 10/1984 | Via . | | 4,937,161 | 6/1990 | Kita et al. . |
| 4,495,041 | 1/1985 | Goldstein ....................... 204/158 R | | 4,942,113 | 7/1990 | Trundle . |
| 4,496,447 | 1/1985 | Eichler et al. . | | 4,952,478 | 8/1990 | Miyagawa et al. ....................... 430/138 |
| 4,510,392 | 4/1985 | Litt et al. . | | 4,952,680 | 8/1990 | Schmeidl . |
| 4,523,924 | 6/1985 | Lacroix . | | 4,954,380 | 9/1990 | Kanome et al. . |
| 4,524,122 | 6/1985 | Weber et al. . | | 4,956,254 | 9/1990 | Washizu et al. . |
| 4,548,896 | 10/1985 | Sabongi et al. . | | 4,968,813 | 11/1990 | Rule et al. . |
| 4,555,474 | 11/1985 | Kawamura . | | 4,985,345 | 1/1991 | Hayakawa et al. . |
| 4,565,769 | 1/1986 | Dueber et al. . | | 4,987,056 | 1/1991 | Imahashi et al. . |
| 4,567,171 | 1/1986 | Mangum . | | 4,997,745 | 3/1991 | Kawamura et al. . |
| 4,571,377 | 2/1986 | McGinniss et al. . | | 5,001,330 | 3/1991 | Koch . |
| 4,595,745 | 6/1986 | Nakano et al. . | | 5,002,853 | 3/1991 | Aoai et al. . |
| 4,604,344 | 8/1986 | Irving et al. . | | 5,002,993 | 3/1991 | West et al. . |
| 4,613,334 | 9/1986 | Thomas et al. . | | 5,003,142 | 3/1991 | Fuller . |
| 4,617,380 | 10/1986 | Hinson et al. . | | 5,006,758 | 4/1991 | Gellert et al. . |
| 4,622,286 | 11/1986 | Sheets . | | 5,013,959 | 5/1991 | Kogelschatz . |
| 4,632,891 | 12/1986 | Banks et al. . | | 5,023,129 | 6/1991 | Morganti et al. . |
| 4,632,895 | 12/1986 | Patel et al. . | | 5,025,036 | 6/1991 | Carson et al. . |
| 4,634,644 | 1/1987 | Irving et al. . | | 5,026,427 | 6/1991 | Mitchell et al. . |
| 4,638,340 | 1/1987 | Iiyama et al. . | | 5,028,792 | 7/1991 | Mullis . |
| 4,663,275 | 5/1987 | West et al. . | | 5,034,526 | 7/1991 | Bonham et al. . |
| 4,663,641 | 5/1987 | Iiyama et al. . | | 5,045,435 | 9/1991 | Adams et al. . |
| 4,668,533 | 5/1987 | Miller . | | 5,045,573 | 9/1991 | Kohler et al. . |

| | | | | | | |
|---|---|---|---|---|---|---|
| 5,053,320 | 10/1991 | Robbillard. | | 5,296,275 | 3/1994 | Goman et al.. |
| 5,055,579 | 10/1991 | Pawlowski et al.. | | 5,296,556 | 3/1994 | Frihart. |
| 5,070,001 | 12/1991 | Stahlhofen. | | 5,300,403 | 4/1994 | Angelopolus et al. ............... 430/1 R |
| 5,076,808 | 12/1991 | Hahn et al.. | | 5,302,195 | 4/1994 | Helbrecht. |
| 5,085,698 | 2/1992 | Ma et al.. | | 5,302,197 | 4/1994 | Wickrammanayke et al.. |
| 5,087,550 | 2/1992 | Blum et al.. | | 5,312,713 | 5/1994 | Yokoyama et al.. |
| 5,089,374 | 2/1992 | Saeva. | | 5,312,721 | 5/1994 | Gesign. |
| 5,096,489 | 3/1992 | Laver. | | 5,324,349 | 6/1994 | Sano et al.. |
| 5,098,806 | 3/1992 | Robillard. | | 5,328,504 | 7/1994 | Ohnishi. |
| 5,106,723 | 4/1992 | West et al.. | | 5,330,860 | 7/1994 | Grot et al.. |
| 5,108,505 | 4/1992 | Moffat. | | 5,334,455 | 8/1994 | Noren et al.. |
| 5,108,874 | 4/1992 | Griffing et al.. | | 5,340,631 | 8/1994 | Matsuzawa et al.. |
| 5,110,706 | 5/1992 | Yumoto et al.. | | 5,340,854 | 8/1994 | Martic et al.. |
| 5,110,709 | 5/1992 | Aoai et al.. | | 5,356,464 | 10/1994 | Hickman et al.. |
| 5,114,832 | 5/1992 | Zertani et al.. | | 5,362,592 | 11/1994 | Murofushi et al. ................ 430/106 |
| 5,124,723 | 6/1992 | Laver. | | 5,372,917 | 12/1994 | Tsuchida et al.. |
| 5,130,227 | 7/1992 | Wade et al.. | | 5,376,503 | 12/1994 | Audett et al.. |
| 5,130,778 | 7/1992 | Shor et al.. | | 5,393,580 | 2/1995 | Ma et al.. |
| 5,133,803 | 7/1992 | Moffatt. | | 5,401,303 | 3/1995 | Stoffel et al.. |
| 5,135,940 | 8/1992 | Belander et al.. | | 5,415,976 | 5/1995 | Zaki. |
| 5,139,572 | 8/1992 | Kawashima. | | 5,426,164 | 6/1995 | Babb et al.. |
| 5,141,556 | 8/1992 | Matrick. | | 5,432,274 | 7/1995 | Luong et al. ..................... 536/103 |
| 5,141,797 | 8/1992 | Wheeler. | | 5,455,143 | 10/1995 | Ali ............................. 430/281 |
| 5,147,901 | 9/1992 | Rutsch et al.. | | | | |

FOREIGN PATENT DOCUMENTS

| | | |
|---|---|---|
| 5,153,104 | 10/1992 | Rossman et al.. |
| 5,153,105 | 10/1992 | Sher et al.. |
| 5,153,166 | 10/1992 | Jain et al.. |
| 5,160,372 | 11/1992 | Matrick. |
| 5,166,041 | 11/1992 | Murofushi et al.. |
| 5,169,436 | 12/1992 | Matrick. |
| 5,169,438 | 12/1992 | Matrick. |
| 5,173,112 | 12/1992 | Matrick et al.. |
| 5,176,984 | 1/1993 | Hipps, Sr. et al.. |
| 5,178,420 | 1/1993 | Shelby. |
| 5,180,425 | 1/1993 | Matrick et al.. |
| 5,180,652 | 1/1993 | Yamaguchi et al.. |
| 5,185,236 | 2/1993 | Shiba et al.. |
| 5,187,045 | 2/1993 | Bonham et al.. |
| 5,187,049 | 2/1993 | Sher et al.. |
| 5,190,565 | 3/1993 | Berenbaum et al.. |
| 5,190,845 | 3/1993 | Hashimoto et al.. |
| 5,196,295 | 3/1993 | Davis. |
| 5,198,330 | 3/1993 | Martic et al.. |
| 5,202,209 | 4/1993 | Winnik et al. ................. 430/106.6 |
| 5,202,210 | 4/1993 | Matsuoka et al. ............. 430/106.6 |
| 5,202,211 | 4/1993 | Vercoulen ....................... 430/109 |
| 5,202,212 | 4/1993 | Shin et al. ...................... 430/109 |
| 5,202,213 | 4/1993 | Nakahara et al. ............... 430/110 |
| 5,202,215 | 4/1993 | Kanakura et al. ............... 430/137 |
| 5,202,221 | 4/1993 | Imai et al.. |
| 5,205,861 | 4/1993 | Matrick. |
| 5,208,136 | 5/1993 | Zanoni et al.. |
| 5,209,814 | 5/1993 | Felten et al.. |
| 5,219,703 | 6/1993 | Bugner et al.. |
| 5,221,334 | 6/1993 | Ma et al.. |
| 5,224,197 | 6/1993 | Zanoni et al.. |
| 5,224,476 | 7/1993 | Schultz et al.. |
| 5,224,987 | 7/1993 | Matrick. |
| 5,241,059 | 8/1993 | Yoshinaga. |
| 5,244,476 | 9/1993 | Schulz et al. ......................... 8/492 |
| 5,250,109 | 10/1993 | Chan et al.. |
| 5,254,429 | 10/1993 | Gracia et al. ..................... 430/162 |
| 5,258,274 | 11/1993 | Helland et al.. |
| 5,262,276 | 11/1993 | Kawamura. |
| 5,268,027 | 12/1993 | Chan et al.. |
| 5,270,078 | 12/1993 | Walker et al.. |
| 5,271,765 | 12/1993 | Ma. |
| 5,272,201 | 12/1993 | Ma et al.. |
| 5,275,646 | 1/1994 | Marshall et al.. |
| 5,279,652 | 1/1994 | Kaufmann et al.. |
| 5,284,734 | 2/1994 | Blum et al.. |
| 5,294,528 | 3/1994 | Furutachi. |

| | | |
|---|---|---|
| 465499 | 5/1950 | Canada. |
| 483214 | 5/1952 | Canada. |
| 517364 | 10/1955 | Canada. |
| 537687 | 3/1957 | Canada. |
| 552565 | 2/1958 | Canada. |
| 571792 | 3/1959 | Canada. |
| 779239 | 2/1968 | Canada. |
| 930103 | 7/1973 | Canada. |
| 2053094 | 4/1990 | Canada. |
| 94118 | 5/1958 | Czechoslovakia. |
| 0127574 | 12/1984 | European Pat. Off.. |
| 0226587 | 5/1987 | European Pat. Off.. |
| 0 223 587 | 5/1987 | European Pat. Off.. |
| 0280458 | 8/1988 | European Pat. Off.. |
| 0308274 | 3/1989 | European Pat. Off.. |
| 0375160 | 6/1990 | European Pat. Off.. |
| 0371304 | 6/1990 | European Pat. Off.. |
| 0390439 | 10/1990 | European Pat. Off.. |
| 0458140A1 | 10/1991 | European Pat. Off.. |
| 0468465 | 1/1992 | European Pat. Off.. |
| 0542286 | 5/1993 | European Pat. Off.. |
| 000571190 | 11/1993 | European Pat. Off.. |
| 463515 | 4/1937 | Germany. |
| 1047787 | 12/1957 | Germany. |
| 1022801 | 1/1958 | Germany. |
| 1039835 | 9/1958 | Germany. |
| 1040562 | 10/1958 | Germany. |
| 1045414 | 12/1958 | Germany. |
| 1047013 | 12/1958 | Germany. |
| 1132540 | 7/1962 | Germany. |
| 1132450 | 7/1962 | Germany. |
| 1154069 | 9/1963 | Germany. |
| 1240811 | 5/1967 | Germany. |
| 2437380 | 2/1975 | Germany. |
| 244520 | 3/1975 | Germany. |
| 2416259 | 10/1975 | Germany. |
| 2714978 | 10/1977 | Germany. |
| 34 15 033 A1 | 10/1984 | Germany. |
| 3921600 | 1/1990 | Germany. |
| 3833437 | 4/1990 | Germany. |
| 3833438 | 4/1990 | Germany. |
| 004036328 | 7/1991 | Germany. |
| 4132288 | 4/1992 | Germany. |
| 662500 | 4/1964 | Italy. |
| 424756 | of 0000 | Japan. |
| 43-15663 | 7/1968 | Japan. |
| 47-26653 | 7/1972 | Japan. |

| | | |
|---|---|---|
| 47-45409 | 11/1972 | Japan . |
| 49-8909 | 2/1974 | Japan . |
| 50-65592 | 6/1975 | Japan . |
| 55-90506 | 7/1980 | Japan . |
| 0014233 | 2/1981 | Japan . |
| 56-14569 | 2/1981 | Japan . |
| 56-36556 | 4/1981 | Japan . |
| 57-61055 | 4/1982 | Japan . |
| 57-128283 | 8/1982 | Japan . |
| 57-171775 | 10/1982 | Japan . |
| 58-125770 | 7/1983 | Japan . |
| 58-211426 | 12/1983 | Japan . |
| 58-222164 | 12/1983 | Japan . |
| 59-89360 | 5/1984 | Japan . |
| 29219270 | 12/1984 | Japan . |
| 59-219270 | 4/1985 | Japan . |
| 60-192729 | 10/1985 | Japan . |
| 60-239739 | 11/1985 | Japan . |
| 60-239740 | 11/1985 | Japan . |
| 60-239741 | 11/1985 | Japan . |
| 60-239743 | 11/1985 | Japan . |
| 61-288 | 1/1986 | Japan . |
| 61-3781 | 1/1986 | Japan . |
| 61-14994 | 1/1986 | Japan . |
| 61-21184 | 1/1986 | Japan . |
| 61-25885 | 2/1986 | Japan . |
| 61-30592 | 2/1986 | Japan . |
| 61-40366 | 2/1986 | Japan . |
| 61-97025 | 9/1986 | Japan . |
| 61-222789 | 10/1986 | Japan . |
| 61-247703 | 11/1986 | Japan . |
| 61-285403 | 12/1986 | Japan . |
| 62-7703 | 1/1987 | Japan . |
| 62-97881 | 5/1987 | Japan . |
| 62-100557 | 5/1987 | Japan . |
| 62-127281 | 6/1987 | Japan . |
| 63-43959 | 2/1988 | Japan . |
| 63-48370 | 3/1988 | Japan . |
| 63-95448 | 4/1988 | Japan . |
| 63-95447 | 4/1988 | Japan . |
| 63-95446 | 4/1988 | Japan . |
| 63-95440 | 4/1988 | Japan . |
| 63-95439 | 4/1988 | Japan . |
| 63-95450 | 4/1988 | Japan . |
| 63-95449 | 4/1988 | Japan . |
| 63-95445 | 4/1988 | Japan . |
| 63-151946 | 6/1988 | Japan . |
| 63-223077 | 9/1988 | Japan . |
| 63-223078 | 9/1988 | Japan . |
| 63-243101 | 10/1988 | Japan . |
| 63-199781 | 12/1988 | Japan . |
| 64-29337 | 1/1989 | Japan . |
| 64-40948 | 2/1989 | Japan . |
| 1-014948 | 3/1989 | Japan . |
| 1128063 | 5/1989 | Japan . |
| 1146974 | 6/1989 | Japan . |
| 1-210477 | 8/1989 | Japan . |
| 01210477 | 8/1989 | Japan . |
| 1288854 | 11/1989 | Japan . |
| 292957 | 4/1990 | Japan . |
| 2179642 | 7/1990 | Japan . |
| 2282261 | 11/1990 | Japan . |
| 03163566 | 7/1991 | Japan . |
| 3-163566 | 7/1991 | Japan . |
| 3-2064369 | 9/1991 | Japan . |
| 5134447 | 11/1991 | Japan . |
| 3284668 | 12/1991 | Japan . |
| 3-203694 | 12/1991 | Japan . |
| 4023884 | 1/1992 | Japan . |
| 4023885 | 1/1992 | Japan . |
| 4-45174 | 2/1992 | Japan . |
| 4100801 | 4/1992 | Japan . |
| 4-136075 | 5/1992 | Japan . |
| 04356087 | 12/1992 | Japan . |
| 543806 | 2/1993 | Japan . |
| 561220 | 3/1993 | Japan . |
| 5080506 | 4/1993 | Japan . |
| 5-134447 | 5/1993 | Japan . |
| 05119506 | 5/1993 | Japan . |
| 5-140498 | 6/1993 | Japan . |
| 2-219869 | 9/1993 | Japan . |
| 5263067 | 10/1993 | Japan . |
| 680915 | 3/1994 | Japan . |
| 6116555 | 4/1994 | Japan . |
| 6116556 | 4/1994 | Japan . |
| 6116557 | 4/1994 | Japan . |
| 6214339 | 8/1994 | Japan . |
| 6256494 | 9/1994 | Japan . |
| 6256633 | 9/1994 | Japan . |
| 7113828 | 4/1972 | Netherlands . |
| 1772118 | 10/1992 | Russian Federation . |
| 603767 | 8/1978 | Switzerland . |
| 197808 | 5/1988 | Switzerland . |
| 1310767 | 5/1987 | U.S.S.R. . |
| 349339 | 5/1931 | United Kingdom . |
| 355686 | 8/1931 | United Kingdom . |
| 399753 | 10/1933 | United Kingdom . |
| 441085 | 1/1936 | United Kingdom . |
| 492711 | 6/1938 | United Kingdom . |
| 518612 | 3/1940 | United Kingdom . |
| 539912 | 9/1941 | United Kingdom . |
| 626727 | 7/1947 | United Kingdom . |
| 600451 | 4/1948 | United Kingdom . |
| 616362 | 1/1949 | United Kingdom . |
| 618616 | 2/1949 | United Kingdom . |
| 779389 | 7/1957 | United Kingdom . |
| 1372884 | 11/1974 | United Kingdom . |
| 2146357 | 4/1985 | United Kingdom . |
| 9211295 | 7/1992 | WIPO . |
| 93/06597 | 4/1993 | WIPO . |
| WO93/06597 | 4/1993 | WIPO . |
| 94/22500 | 10/1994 | WIPO . |
| 94/22501 | 10/1994 | WIPO . |

OTHER PUBLICATIONS

Hosokawa et al., "Ascofuranone, an antibiotic from Asochyta," Japan Kokai 73 91,278 (Nov. 28, 1983), *Merck Index*, 80:p. 283; abstract 94259t (1974).

Maki, Y. et al. "A Novel heterocyclic N–oxide, pyrimido[5,4–g]pteridinetetrone 5–oxide, with multifunctional" *Chemical Abstracts* 122 925 [No. 122:31350F] 1995.

Abstract of patent, JP 0643573 1994.

Pitchumani, K. et al. "Modification of chemical reactivity upon cyclodextrin encapsulation " *Chemical Abstracts* 121 982[No. 121:133634v] 1994.

Derwent Publications Ltd., London, 1993 JP 05297627 (Fujitsu Ltd.), Nov. 12, 1993. (Abstract) 1993.

Patent Abstracts of Japan, JP 5241369 (Bando Chem Ind Ltd et al.), Sep. 21, 1993. (Abstract) 1993.

Derwent Publications Ltd., London, JP 05232738 (Yamazaki, T.), Sep. 10, 1993. (Abstract) 1993.

Derwent Publications Ltd., London, EP 000559310 (Zeneca Ltd.), Sep. 8, 1993. (Abstract) 1993.

Derwent Publications Ltd., London, J,A, 5–230410 (Seiko Epson Corp), Sep. 7, 1993. (Abstract) 1993.

Derwent Publications Ltd., London, JP 5–230407 (Mitsubishi Kasei Corp), Sep. 7, 1993. (Abstract) 1993.

Patent Abstracts of Japan, JP 5197198 (Bando Chem Ind Ltd et al.), Aug. 6, 1993. (Abstract) 1993.

Database WPI—Week 9336, Derwent Publications Ltd., London, J,A, 5197069 (Bando Chem), Aug. 6, 1993.

Patent Abstracts of Japan, JP5181308 (Bando Chem Ind Ltd et al.), Jul. 23, 1993. (Abstract) 1993.
Patent Abstracts of Japan, JP 5181310 (Bando Chem Ind Ltd et al.), Jul. 23, 1993. (Abstract) 1993.
Derwent Publications Ltd., London, JP 5–132638 (Missubishi Kasei Corp), May 28, 1993. (Abstract) 1993.
Derwent Publications Ltd., London, JP 5–125318 (Mitsubishi Kasei Corp), May 21, 1993. (Abstract). 1993.
Abstract of patent, JP 05 117200 1993.
Derwent Publications Ltd., London, JP 05061246 (Ricoh KK), Mar. 12, 1993. (Abstract) 1993.
Duxbury "The Photochemistry and Photophysics of Triphenylmethane Dyes in Solid Liquid Media" Chemical Review 93 381–433 1993.
Abstract of patent, JP 04351603 1992.
Abstract of patent, JP 04351602 1992.
Derwent Publications Ltd., London, JP 4–314769 (Citizen Watch Co Ltd), Nov. 5, 1992. (Abstract) 1992.
Abstract of patent, JP 04315739 1992.
Derwent Publications Ltd., London, JP 04300395 (Funai Denki KK), Oct. 23, 1992. (Abstract) 1992.
Derwent Publications Ltd., London, JP 4–213374 (Mitsubishi Kasei Corp), Aug. 4, 1992. (Abstract) 1992.
Abstract of patent, JP 04210228 1992.
Derwent Publications Ltd., London, J,P, 4–202271 (Mitsubishi Kasei Corp), Jul. 23, 1992. (Abstract) 1992.
Derwent Publications Ltd., London, J,A, 4–202571 (Canon Inc.), Jul. 23, 1992. (Abstract) 1992.
Derwent Publications Ltd., London, JP 4–189877 (Seiko Epson Corp), Jul. 8, 1992. (Abstract) 1992.
Derwent Publications Ltd., London, JP 4–189876 (Seiko Epson Corp), Jul. 8, 1992. (Abstract) 1992.
Derwent Publications Ltd., London, J,A, 4–170479 (Seiko Epson Corp), Jun. 18, 1992. (Abstract) 1992.
Abstract of patent, JP 0481402 1992.
Abstract of patent, JP 0481401 1992.
Derwent Publications Ltd., London, J0 3247676 (Canon KK), Nov. 5, 1991. (Abstract) 1991.
Abstract of patent, JP 03–220384 1991.
Derwent Publications Ltd., London, JP 3167270 (Mitsubishi Kasei Corp), Jul. 19, 1991. (Abstract) 1991.
Derwent Publications Ltd., London, J0 3093870 (Dainippon Ink Chem KK), Apr. 18, 1991. (Abstract) 1991.
Abstract of patent, JP 06369890 1991.
Abstract of patent, JP 03 41165 1991.
Braithwaite, M., et al. "Formulation" Chemistry & Technology of UV & EB Formulation for Coatings, Inks & Paints IV 11–12 1991.
Scientific Polymer Products, Inc. Brochure 24–31 1991.
Dietliker, K. "Photoiniators for Free Radical and Catioinc Polymerisation" Chemistry & Technology of UV & EB Formulation for Coatings, Inks & Paints III 1991.
Abstract of patent, JP 02289652 1990.
Abstract of Patent, JP 0297957, (Fuji Xerox Co., Ltd.) 1990.
Derwent Publications Ltd., London, JP 2091166 (Canon KK), Mar. 30, 1990. (Abstract) 1990.
Kogelschatz, U. "Silent Discharges for the Generation of ultraviolet and vacuum ultraviolet excimer radiation" Pure & Applied Chem. 62 1667–74 1990.
Abstract of patent, JP 01299083 1989.
Derwent Publications Ltd., London, J,0, 1182379 (Canon KK), Jul. 20, 1989. (Abstract) 1989.
Derwent Publications Ltd., London, J,0, 1011171 (Mitsubishi Chem Ind KK), Jan. 13, 1989. (Abstract) 1989.

"Xerographic Materials" Encyclopedia of Polymer Science and Engineering 17 918–943 1989.
Pappas, S.P. "Photocrosslinking" Comph. Pol. Sci. 6 135–148 1989.
Pappas, S.P. "Photoinitiated Polymerization" Comph. Pol. Sci. 4 337–355 1989.
Kirilenko, G.V. "An analog of the vesicular process with amplitude modulation of the incident light beam" Chemical Abstracts 111 569 [No. 111:123633b] 1989.
Abstract of patent, JP 63190815 1988.
Abstract of patent, JP 63144329 1988.
Abstract of patent, JP 63130164 1988.
Abstract of patent, JP 6177846 1988.
Abstract of patent, JP 63732241 1988.
Abstract of patent, JP 6347762, 1988.
Abstract of patent, JP 63 47763, 1988.
Abstract of patent, JP 63–47764, 1988.
Abstract of patent, JP 63–47765, 1988.
Eliasson, B., et al. "UV Excimer Radiation from Dielectric–Barrier Discharges" Applied Physics B 46 299–303 1988.
Abstract of patent, JP 62215261 1987.
Abstract of patent, JP 6232082 1987.
Derwent Publications Ltd., London, J6 2007772 (Alps Electric KK), Jan. 14, 1987. (Abstract) 1987.
Derwent Publications Ltd., London, JA 0284478 (Sanyo Chem Ind Ltd), Dec. 15, 1986. (Abstract) 1986.
Abstract of patent, JP 61251842 1986.
Abstract of patent, JP 6197025 1986.
Abstract of patent, JP 6187760 1986.
Derwent Publications Ltd., London, DL 0234731 (Karl Marx Univ. Leipzig), Apr. 9, 1986. (Abstract) 1986.
Derwent Publications Ltd., London, J, 0226575 (Sumitomo Chem Ind KK), Oct. 11, 1985. (Abstract) 1985.
Abstract of patent, JP 60156761 1985.
Derwent Publications Ltd., London, J,A, 0011451 (Fugi Photo Film KK), Jan. 21, 1985. (Abstract) 1985.
Roos, G. et al. "Textile applications of photocrosslinkable polymers" Chemical Abstracts 103 57[No. 103:23690j] 1985.
Derwent Publications Ltd., London, JP 0198187 (Canon KK), Nov. 9, 1984. (Abstract) 1984.
Derwent Publications Ltd., London, J,A, 0169883 (Ricoh KK), Sep. 25, 1984. (Abstract) 1984.
Derwent Publications Ltd., London, J,A, 0053563 (Dainippon Toryo KK), Mar. 28, 1984 (Abstract) 1984.
Derwent Publications Ltd., London, J,A, 0053562 (Dainippon Toryo KK), Mar. 28, 1984. (Abstract) 1984.
Derwent Publications Ltd., London, J,A, 0051961 (Dainippon Toryo KK), Mar. 26, 1984). (Abstract) 1984.
Saenger, W. "Structural Aspects of Cyclodextrins and Their Inclusion Complexes" Inclusion Compounds—Structural Aspects of Inclusion Compounds 2 231–259 1984.
Szejtli "Industrial Applications of Cyclodextrins" Inclusion Compounds: Physical Prop. & Applns 3 331–390 1984.
"Clathrate Compounds, Molecular Inclusion Phenomena, and Cyclodextrins" D. Reidel Publishing 714–746 1984.
van Beek, H.C.A "Light–Induced Colour Changes in Dyes and Materials" Color Res. and Appl. 8 176–181 1983.
Connors, K.A. "Application of a stoichiometric model of cyclodextrin complex formation" Chemical Abstracts 98 598[No. 98:53067g] 1983.
Derwent Publications Ltd., London, EP 0065617 (IBM Corp.), Dec. 1, 1982. (Abstract) 1982.

Derwent Publications Ltd., London, J,A, 0187289 (Honshu Paper Mfg KK), Nov. 17, 1982. (Abstract) 1982.
Derwent Publications Ltd., London, JA 0185364 (Ricoh KK), Nov. 15, 1982. (Abstract) 1982.
Derwent Publications Ltd., London, J,A, 0090069 (Canon KK), Jun. 4, 1982. (Abstract) 1982.
Derwent Publications Ltd., London, J,A, 0010661 (Canon KK), Jan. 20, 1982. (Abstract) 1982.
Derwent Publications Ltd., London, J,A, 0010659 (Canon KK), Jan. 20, 1982. (Abstract) 1982.
Derwent Publications Ltd., London, J,A, 0155263 (Canon KK), Dec. 1, 1981. (Abstract) 1981.
Derwent Publications Ltd., London, J,A, 0147861 (Canon KK), Nov. 17, 1981. (Abstract) 1981.
Derwent Publications Ltd., London, J,A, 0143273 (Canon KK), Nov. 17, 1981. (Abstract) 1981.
Derwent Publications Ltd., London, J,A, 0136861 (Canon KK), Oct. 26, 1981. (Abstract) 1981.
Derwent Publications Ltd., London, J,A, 6133378 (Canon KK), Oct. 19, 1981 (Abstract) 1981.
Derwent Publications Ltd., London, J,A, 6133377 (Canon KK), Oct. 19, 1981. (Abstract) 1981.
Derwent Publications Ltd., London, J,A, 6093775 (Canon KK), Jul. 29, 1981. (Abstract) 1981.
Derwent Publications Ltd., London, J,A, 0008135 (Ricoh KK), Jan. 27, 1981. (Abstract) 1981.
Derwent Publications Ltd., London, J,A, 0004488 (Canon KK), Jan. 17, 1981. (Abstract) 1981.
Rosanske et al. "Stoichiometric Model of Cyclodextrin Complex Formation" *Journal of Pharmaceutical Sciences* 69 (5) 564–567 1980.
Derwent Publications Ltd., London, J,A, 0005422 (Fuji Photo Film KK), Jan. 16, 1979 (Abstract) 1979.
"Color imaging devices and color filter arrays using photo–bleachable dyes" *Research Disclosure* 22–23 1979.
"Electrophotography" *Kirk–Othmer Encyclopedia of Chemical Technology* 3rd ed., vol 8, Wiley Interscience, New York, pp. 794–826 1979.
Derwent Publications Ltd., London, J,A, 0012037 (Pentel KK), Jan. 29, 1977. (Abstract) 1977.
"Photo–bleachable dyes and processes" *Research Disclosure* 85–87 1975.
Jenkins, P.W. et al. "Photobleachable dye material" *Research Disclosure* 18[No. 12932] 1975.
Lamberts, R.L. "Recording color grid patterns with lenticules" *Research Disclosure* 18–19 [No. 12923] 1975.
Karmanova, L.S. et al. "Light stabilizers of daytime fluorescent paints" *Chemical Abstracts* 82 147 [No. 59971p] 1975.
Prokopovich, B. et al. "Selection of effective photoinducers for rapid hardening of polyester varnish PE–250" *Chemical Abstracts* 83 131 [No. 81334a] 1975.
"Variable Contrast Printing System" *Research Disclosure* 19 [No. 12931] 1975.
Chang, I.F., et al. "Color Modulated Dye Ink Jet Printer" *IBM Technical Disclosure Bulletin* 17(5) 1520–1521 1974.
"Darocur 1173: Liquid Photoiniator for Ultraviolet Curing of Coatings" 1974.
Fischer, "Submicroscopic contact imaging with visible light by energy transfer".
Chatterjee, S. et al. "Photochemistry of Carbocyanine Alkyltriphenylborate Salts: Intra–Ion–Pair Electron Transfer and the Chemistry of Boranyl Radicals", J. Am. Chem. Soc., vol. 112, No. 17, pp. 6329–6338. 1990.

"Assay—Physical and Chemical Analysis of Complexes" *AMAIZO*.
"Cyclodextrin" *AMAIZO*.
"Beta Cyclodextrin Polymer (BCDP)" *AMAIZO*.
"Chemically Modified Cyclodextrins" *AMAIZO*.
"Cyclodextrin Complexation" *American Maize Products Co.*
"Cyclodextrins: A Breakthrough for Molecular Encapsulation" *American Maize Products Co. (AMAIZO)* 1993.
"Monomers" *Scientific Polymer Products Inc.*
Suppan, Paul "Quenching of Excited States" *Chemistry and Light* 65–69.
Yamaguchi, H. "Supersensitization. Aromatic ketones as supersensitizers" *Chemical Abstracts* 53 107 (d).
Stecher, H. "Ultraviolet–absorptive additives in adhesives, lacquers and plastics" *Chemical Abstracts* 53 14579 (c).
Maslennikov, A.S. "Coupling of diazonium salts with ketones" *Chemical Abstracts* 60 3128e.
Derwent Publications, Ltd., London SU 292698–S Jan. 15, 1871 (abstract).
Derwent Publication, Ltd., London, JA 7226653.
Derwent Publications Ltd., London, 2416259.
Derwent Publications Ltd., London, 4 9128022.
Derwent Publications Ltd., London, 47 45409.
Derwent Publications, Ltd., London, 7112489.
Derwent Publications, Ltd., London, J6 2270665 (Konishiroku Photo KK), Nov. 25, 1987 (Abstract).
Derwent Publications, Ltd., London, EP 0280653, Aug. 31, 1988 (Abstract).
Derwent Publications, Ltd., London, SU 1423656 (Kherson Ind Inst), Sep. 15, 1988 (Abstract).
Abstract of Patent, JP 405195450.
Derwent Publications, Ltd., London, J6 1041381 (Osaka Prefecture Feb. 27, 1986 (Abstract).
Derwent Publications, Ltd., London, JA 0061785 (Nippon Senka KK), Apr. 14, 1982 (Abstract).
Derwent Publications, Ltd., London, EP 0072775 (Ciba Geigy AG, Feb. 23, 1983 (Abstract).
Derwent Publications, Ltd., London, J6 3108074 (Konishiroku Photo KK), May 12, 1988 (Abstract).
Derwent Publications, Ltd., London, J6 3108073 (Konishiroku Photo KK), May 12, 1988 (Abstract).
Derwent Publications, Ltd., London, J6 3112770 (Toray Ind Inc), May 17, 1988 (Abstract).
Derwent Publications, Ltd., London, JP 403269167 (Japan Wool Textile KK), Nov. 29, 1991 (Abstract).
Gafney et al. Photochemical Reactions of Copper (II)—1, 3–Diketonate Complexes *Journal of the Americqal Chemical Society.*
Gross et al. Laser direct–write metallization in thin palladium acetate films *J. App. Phys.* 61 (4) 1628–1632.
Al–Ismail et al. Some experimental results on thin polypropylene films loaded with finely–dispersed copper *Journal of Materials Science* 415–418.
Baufay et al. Oprtical self–regulation during laser–induced oxidation of copper *J. Appl. Phys* 61 (9) 4640–4651.
Esrom et al. Large area Photochemical Dry Etching of Polymers iwth Incoherent Excimer UV Radiation *MRS Materials Research Society* 1–7.
Derwent Publications, Ltd., London CA, 1086–719, (Sherwood Medical) Sep. 3, 1980 (Abstract).
New Excimer UV Sources for Industrial Applications *ABB Review* 391 1–10.
Kogelschatz Silent–discharge driven excimer UV sources and their applications *Applied Surface Science* 410–423.

Eliasson et al. New Trends in High Intensity UV Generation *EPA Newsletter* (32) 29–40.

Esrom et al. Excimer Laser–Induced Decomposition of Aluminum Nitride *Materials Research Society Fall Meeting* 1–6.

Esrom et al. Investigatin of the mechanism of the UV–induced palladium depostions processf from thin solid *Applied Surface Science* 46 158–162.

Kogelschatz et al. New Incoherent Ultraviolet Excimer Sources for Photolytic Material Deposition.

Esrom et al. Metal deposition with a windowless VUV excimer source *Applied Surface Science* 1–5.

Esrom et al. UV excimer laser–induced pre–nucleation of surfaces followed by electroless metallization *Chemtronics* 4 216–223.

Esrom Excimer Laser–Induced Surface Activation of Aln for Electroless Metal Deposition *Mat. Res. Sco.lSymp. Proc.* 204 457–465.

Zhang et al. UV–induced decomposition of adsorbed Cu–acetylacetonate films at room temperature for electroless *Applied Surface Science* 1–6.

Esrom et al. VUV light–induced deposition of palladium using an incoherent Xe2* excimer source *Chemtronics* 4.

Lakshman Electronic Absorption Spectrum of Copper Formate Tetrahydrate *Chemical Physics Letters* 31 (2) 331–334.

Esrom et al. UV Light–Induced Depostion of Copper Films C5–719–C5–725.

Esrom et al. Metal Deposition with Incoherent Excimer Radiation *mat. Res. Soc. Symp. Proc.* 158 189–198.

Zhang et al. VUV synchrotron radiation processing of thin palladium acetate spin–on films for metallic surface *Applied Surface Science* 46 153–157.

Esrom UV Excimer Laer–Induced Deposition of Palladium from palladiym Acetate Films *Mat. Res. Soc. Symp. Proc.* 158 109–117.

German company develops reuseable paper *Pulp & Paper.*

Derwent Publications, Ltd., London J6 0011–449–A (Taoka Chemical KK) Jan. 21, 1985 (abstract).

Derwent Publications, Ltd., London J5 7139–146 (Showa Kako KK) Aug. 27, 1982 (abstract).

Derwent Publications, Ltd., London J4 9131–226 (TNational Cash Register C) Dec. 16, 1974 (abstract).

Derwent Publications, Ltd., London CA 1086–719 (Sherwood Medical) Sep. 30, 1980 (abstract).

"Encyclopedia of Polymer Science and Engineering", vol. 17, Wiley Interscience, New York, pp. 918–943. 1989.

N. Husain et al., "Cyclodextrins as mobile–phase additives in reversed–phase HPLC—An Overview", American Laboratory, vol. 82, pp. 80–87. Oct. 1993.

"Coloring/Decoloring Agent For Toner Use Developed", Japan Chemical Week. Jun. 20, 1991.

J. Rigdon, "In Search of Paper That Spies Can'Copy", The Wall Street Journal. Unknow.

D. Hamilton, "Tired of Shredding? New Ricoh Method Tries Different Tack", The Wall Street Journal, p. b2 Aug. 20, 1993.

ELECTROPHOTGRAPHIC PROCESS UTILIZING MUTABLE COLORED COMPOSITION

This is a continuation of application Ser. No. 08/393,089, filed Feb. 22, 1995, which is a continuation of application Ser. No. 08/103,503, filed Aug. 5, 1993, now abandoned.

BACKGROUND OF THE INVENTION

The present invention relates to a solid colored composition, which in some embodiments may be employed as an electrophotographic toner, e.g., a toner employed in a photocopier which is based on transfer xerography.

Electrophotography is broadly defined as a process in which photons are captured to create an electrical image analogue of the original. The electrical analogue in turn is manipulated through a number of steps which result in a physical image. The most commonly used form of electrophotography presently in use is called transfer xerography. Although first demonstrated by C. Carlson in 1938, the process was slow to gain acceptance. Today, however, transfer xerography is the foundation of a multibillion dollar industry.

The heart of the process is a photoreceptor, usually the moving element of the process, which is typically either drum-shaped or a continuous, seamless belt. A corona discharge device deposits gas ions on the photoreceptor surface. The ions provide a uniform electric field across the photoreceptor and a uniform charge layer on its surface. An image of an illuminated original is projected through a lens system and focused on the photoreceptor. Light striking the charged photoreceptor surface results in increased conductivity across the photoreceptor with the concomitant neutralization of surface charges. Unilluminated regions of the photoreceptor surface retain their charges. The resulting pattern of surface charges is the latent electrostatic image.

A thermoplastic pigmented powder or toner, the particles of which bear a charge opposite to the surface charges on the photoreceptor, is brought close to the photoreceptor, thereby permitting toner particles to be attracted to the charged regions on the photoreceptor surface. The result is a physical image on the photoreceptor surface consisting of electrostatically held toner particles.

A sheet of plain paper is brought into physical contact with the tonerbearing photoreceptor. A charge applied to the back side of the paper induces the attraction of the toner image to the paper. The image is a positive image of the original. The paper then is stripped from the photoreceptor, with the toner image clinging to it by electrostatic attraction. The toner image is permanently fused to the paper by an appropriate heating means, such as a hot pressure roll or a radiant heater.

Because there is incomplete transfer of toner to the paper, it is necessary to clean the photoreceptor surface of residual toner. Such toner is wiped off with a brush, cloth, or blade. A corona discharge or reverse polarity aids in the removal of toner. A uniform light source then floods the photoreceptor to neutralize any residual charges from the previous image cycle, erasing the previous electrostatic image completely and conditioning the photoreceptor surface for another cycle.

The toner generally consists of 1-15 micrometer average diameter particles of a thermoplastic powder. Black toner typically contains 5-10 percent by weight of carbon black particles of less than 1 micrometer dispersed in the thermoplastic powder. For toners employed in color xerography, the carbon black may be replaced with cyan, magenta, or yellow pigments. The concentration and dispersion of the pigment must be adjusted to impart a conductivity to the toner which is appropriate for the development system. For most development processes, the toner is required to retain for extended periods of time the charge applied by contact electrification. The thermoplastic employed in the toner in general is selected on the basis of its melting behavior. The thermoplastic must melt over a relatively narrow temperature range, yet be stable during storage and able to withstand the vigorous agitation which occurs in xerographic development chambers.

The success of electrophotography, and transfer xerography in particular, no doubt is a significant factor in the efficient distribution of information which has become essential in a global setting. It also contributes to the generation of mountains of paper which ultimately must either be disposed of or recycled. While paper is recycled, it presently is converted to pulp and treated to remove ink, toner, and other colored materials, i.e., deinked, an expensive and not always completely successful operation. Moreover, deinking results in a sludge which typically is disposed of in a landfill. The resulting deinked pulp then is used, often with the addition of at least some virgin pulp, to form paper, cardboard, cellulosic packaging materials, and the like.

The simplest form of recycling, however, is to reuse the paper intact, thus eliminating the need to repulp. To this end, toners for copier machines have been reported which are rendered colorless on exposure to near infrared or infrared radiation. Although the spectrum of sunlight ends at about 375 nanometers, it has a significant infrared component. Hence, such toners have a salient disadvantage in that they are transitory in the presence of such environmental factors as sunlight and heat; that is, such toners become colorless. This result is unsatisfactory because the documents can be rendered illegible before their function or purpose has ended. Accordingly, there is a need for toners for copy machines which will permit the recycling of paper intact, but which are stable to normally encountered environmental factors.

SUMMARY OF THE INVENTION

It is an object of the present invention to provide a solid colored composition which is adapted to become colorless upon exposure to ultraviolet radiation.

This and other objects will be apparent to those having ordinary skill in the art from a consideration of the specification and claims which follow.

Accordingly, the present invention provides a solid colored composition which includes:

(A) a colorant which, in the presence of an ultraviolet radiation transorber, is adapted, upon exposure of the transorber to ultraviolet radiation, to be mutable; and (B) an ultraviolet radiation transorber which is adapted to absorb ultraviolet radiation and interact with the colorant to effect the irreversible mutation of the colorant.

The present invention also provides a solid colored composition adapted to be utilized as a toner in an electrophotographic process, which composition includes:

(A) a colorant which, in the presence of an ultraviolet radiation transorber, is adapted, upon exposure of the transorber to ultraviolet radiation, to be mutable;

(B) an ultraviolet radiation transorber which is adapted to absorb ultraviolet radiation and interact with the colorant to effect the irreversible mutation of the colorant; and (C) a carrier for the; colorant and the ultraviolet radiation transorber.

The present invention additionally provides a method of mutating a solid colored composition which includes:

(A) providing a colorant which, in the presence of an ultraviolet radiation transorber, is adapted, upon exposure of the transorber to ultraviolet radiation, to be mutable;

(B) providing an ultraviolet radiation transorber which is adapted to absorb ultraviolet radiation and interact with said colorant to effect the irreversible mutation of the colorant;

(C) blending the colorant and the ultraviolet radiation transorber; and (D) irradiating the solid colored composition with ultraviolet radiation at a dosage level sufficient to irreversibly mutate the colorant.

The present invention further provides an electrophotographic process which includes:

(A) creating an image of a pattern on a photoreceptor surface;

(B) applying a toner to the photoreceptor surface to form a toner image which replicates the pattern;

(C) transferring the toner image to a substrate; and (D) fixing the toner image to the substrate; in which the toner includes a colorant, an ultraviolet radiation transorber, and a carrier as already described.

The present invention still further provides an electropho-tographic process which includes:

(A) providing a substrate having a first pattern thereon which is formed by a first toner which includes:

(1) a colorant which, in the presence of an ultraviolet radiation transorber, is adapted, upon exposure of the transorber to ultraviolet radiation, to be mutable;

(2) an ultraviolet radiation transorber which is adapted to absorb ultraviolet radiation and interact with the colorant to effect the irreversible mutation of the colorant; and (3) a carrier for the colorant and the ultraviolet radiation transorber;

(B) exposing the first pattern on the substrate to ultraviolet radiation at a dosage level sufficient to irreversibly mutate the colorant;

(C) creating an image of a second pattern on a photoreceptor surface;

(D) applying a second toner to the photoreceptor surface to form a toner image which replicates the second pattern;

(E) transferring the second toner image of the second pattern to the substrate; and (F) fixing the second toner image to the substrate. If desired, the second toner can be similar to the first toner.

In certain embodiments, the ultraviolet radiation will have a wavelength in the range of from about 100 to about 400 nanometers. In other embodiments, the ultraviolet radiation is incoherent, pulsed ultraviolet radiation from a dielectric barrier discharge excimer lamp.

DETAILED DESCRIPTION OF THE INVENTION

The term "composition" and such variations as "solid colored composition" and "colored composition" are used herein to mean a colorant and an ultraviolet radiation transorber. When reference is being made to a solid colored composition which is adapted for a specific application, such as a toner to be used in an electrophotographic process, the term "composition-based" is used as a modifier to indicate that the material, e.g., a toner, includes a colorant and an ultraviolet radiation transorber.

As used herein, the term "colorant" is meant to include, without limitation, any material which, in the presence of an ultraviolet radiation transorber, is adapted upon exposure to ultraviolet radiation to be mutable. As a practical matter, the colorant typically will be an organic material, such as an organic dye or pigment, including toners and lakes. Desirably, the colorant will be substantially transparent to, that is, will not significantly interact with, the ultraviolet radiation to which it is exposed. The term is meant to include a single material or a mixture of two or more materials.

Organic dye classes include, by way of illustration only, triaryl methyl dyes, such as Malachite Green Carbinol base {4-(dimethylamino)-α-[4-(dimethylamino)phenyl]-α-phenylbenzenemethanol}, Malachite Green Carbinol hydrochloride {N-4-[[4-(dimethylamino)phenyl]phenylmethylene]-2,5-cyclo-hexyldien-1-ylidene]-N-methylmethanaminium chloride or bis[p-(dimethyl-amino)phenyl]phenylmethylium chloride}, and Malachite Green oxalate {N-4-[[4-(dimethylamino)phenyl]phenylmethylene]-2,5-cyclohexyldien- 1 -ylidene]-N-methylmethanaminium chloride or bis[p-(dimethylamino)phenyl]phenyl-methylium oxalate}; monoazo dyes, such as Cyanine Black, Chrysoidine [Basic Orange 2; 4-(phenylazo)-1,3-benzenediamine monohydrochloride], and β-Naphthol Orange; thiazine dyes, such as Methylene Green, zinc chloride double salt [3,7-bis(dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazinocarbonyl)amino]-2,3-dihydro-1,3-dioxo-1H-benz[de]isoquinoline-5,8-disulfonic acid dilithium salt}; azine dyes, such as Janus Green B {3- (diethylamino)-7-[[4-(dimethylamino)phenyl]azo]-5-phenylphenazinium chloride}; cyanine dyes, such as Indocyanine Green {Cardio-Green or Fox Green; 2-[7-[1,3-dihydro-1,1 -dimethyl-3-(4-sulfobutyl)-2H-benz[e]indol-2-ylidene]-1,3,5-heptatrienyl]-1,1 -dimethyl-3-(4-sulfobutyl)-1H-benz[e]indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methylcoumarin (4-methylumbel-liferone); benzimidazole dyes, such as Hoechst 33258 [bisbenzimide or 2'-(4-hydroxyphenyl)-5-(4-methyl- 1 -piperazinyl)-2,5'-bi-1H-benzimidazole trihydrochloride pentahydrate]; paraquinoidal dyes, such as Hematoxylin {Natural Black 1; 7,11b-dihydrobenz[b]indeno[1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxybenzene diazonium chloride, zinc chloride double salt); phenylenediamine dyes, such as Disperse Yellow 9 [N-(2,4-dinitrophenyl)-1,4-phenylenediamine or Solvent Orange 53]; disazo dyes, such as Disperse Orange 13 [Solvent Orange 52; 1-phenylazo-4-(4-hydroxyphenylazo)-naphthalene]; anthraquinone dyes, such as Disperse Blue 3 [Celliton Fast Blue FFR; 1-methylamino-4-(2-hydroxyethylamino)-9,10-anthraquinone], Disperse Blue 14

[Celliton Fast Blue B; 1,4-bis(methylamino)-9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-1-hydroxy-3-sulfo-2-naphthalenyl)azo]-6-sulfo-1-naphthalenyl)azo]-1 -naphthalenyl)azo]-1,5-naphthalenedisulfonic acid tetrasodium salt}; xanthene dyes, such as 2',7'-dichlorofluorescein; proravine dyes, such as 3,6-diaminoacridine hemisulfate (Proflavine); sulfonephthalein dyes, such as Cresol Red (o-cresol-sulfonephthalein); phthalocyanine dyes, such as Copper Phthalocyanine {Pigment Blue 15; (SP-4-1)-[29H, 31H-phthalocyanato(2-)-$N^{29},N^{30},N^{31},N^{32}$]-copper}; carotenoid dyes, such as trans-β-carotene (Food Orange 5); carminic acid dyes, such as Carmine, the aluminum or calcium-aluminum lake of carminic acid (7-α-D-glucopyranosyl-9,10-dihydro-3,5,6,8-tetrahydroxy-1-methyl-9, 10-dioxo-2-anthracenecarboxylic acid); azure dyes, such as Azure A [3-amino-7-(dimethylamino)phenothiazin-5-ium chloride or 7-(dimethylamino)-3-imino-3H-phenothiazine hydrochloride]; and acridine dyes, such as Acridine Orange [Basic Orange 14; 3,8-bis(dimethylamino)acridine hydrochloride, zinc chloride double salt] and Acriflavine (Acriflavine neutral; 3,6-diamino-10-methylacridinium chloride mixture with 3,6-acridinediamine).

The term "mumble" with reference to the colorant is used to mean that the absorption maximum of the colorant in the visible region of the electromagnetic spectrum is capable of being mutated or changed by exposure to ultraviolet radiation when in the presence of the ultraviolet radiation transorber. In general, it is only necessary that such absorption maximum be mutated to an absorption maximum which is different from that of the colorant prior to exposure to the ultraviolet radiation, and that the mutation be irreversible. Thus, the new absorption maximum can be within or without the visible region of the electromagnetic spectrum. In other words, the colorant can mutate to a different color or be rendered colorless. The latter, of course, is desirable when the colorant is used in a solid colored composition adapted to be utilized as a toner in an electrophotographic process which reuses the electrophotographic copy by first rendering the colored composition colorless and then placing a new image thereon.

As used herein, the term "irreversible" means only that the colorant will not revert to its original color when it no longer is exposed to ultraviolet radiation. Desirably, the mutated colorant will be stable, i.e., not appreciably adversely affected by radiation normally encountered in the environment, such as natural or artificial light and heat. Thus, desirably a colorant rendered colorless will remain colorless indefinitely.

The term "ultraviolet radiation transorber" is used herein to mean any material which is adapted to absorb ultraviolet radiation and interact with the colorant to effect the mutation of the colorant. In some embodiments, the ultraviolet radiation transorber may be an organic compound. The term "compound" is intended to include a single material or a mixture of two or more materials. If two or more materials are employed, it is not necessary that all of them absorb ultraviolet radiation of the same wavelength.

While the mechanism of the interaction of the ultraviolet radiation transorber with the colorant is not totally understood, it is believed that it may interact with the colorant in a variety of ways. For example, the ultraviolet radiation transorber, upon absorbing ultraviolet radiation, may be converted to one or more free radicals which interact with the colorant. Such free radical-generating compounds typically are hindered ketones, some examples of which are benzildimethyl ketal (available commercially as Irgacure®651, Ciba-Geigy Corporation, Hawthorne, N.Y.), 1-hydroxycyclohexyl phenyl ketone (Irgacure®500), 2-methyl-1-[4-(methylthio)phenyl]-2-morpholino-propan-1-one](Irgacure®907), 2-benzyl-2-dimethylamino-1-(4-morpholinophenyl)butan-1-one (Irgacure®369), and 1-hydroxycyclohexyl phenyl ketone (Irgacure®184).

Alternatively, the ultraviolet radiation may initiate an electron transfer or reduction-oxidation reaction between the ultraviolet radiation transorber and the colorant. In this case, the ultraviolet radiation transorber may be Michler's ketone (p-dimethylaminophenyl ketone) or benzyl trimethyl stannate. Or, a cationic mechanism may be involved, in which case the ultraviolet radiation transorber could be, for example, bis[4-(diphenylsulphonio)phenyl)] sulfide bis (hexafluorophosphate) (Degacure®KI85, Ciba-Geigy Corporation, Hawthorne, N.Y.); Cyracure®UVI-6990 (Ciba-Geigy Corporation), which is a mixture of bis[4-(diphenylsulphonio)phenyl] sulfide bis (hexafluorophosphate) with related monosulphonium hexafluorophosphate salts; and ($n^5$-2,4-cyclopentadien-1-yl) [(1,2,3,4,5,6-n)-(1-methylethyl)benzene]iron(1+), hexafluorophosphate (Irgacure®261).

The term "ultraviolet radiation" is used herein to mean electromagnetic radiation having wavelengths in the range of from about 100 to about 400 nanometers. Thus, the term includes the regions commonly referred to as ultraviolet and vacuum ultraviolet. The wavelength ranges typically assigned to these two regions are from about 180 to about 400 nanometers and from about 100 to about 180 nanometers, respectively.

In some embodiments, the molar ratio of ultraviolet radiation transorber to colorant generally will be equal to or greater than about 0.5. As a general rule, the more efficient the ultraviolet radiation transorber is in absorbing the ultraviolet radiation and interacting with, i.e., transferring absorbed energy to, the colorant to effect irreversible mutation of the colorant, the lower such ratio can be. Current theories of molecular photochemistry suggest that the lower limit to such ratio is 0.5, based on the generation of two free radicals per photon. As a practical matter, however, higher ratios are likely to be required, perhaps as high as about 50. At the present time, ratios of about 20 to about 30 appear to be typical. In any event, the present invention is not bound by any specific lower molar ratio range. The important feature is that the transorber is present in an amount sufficient to effect mutation of the colorant.

As a practical matter, both the colorant and the ultraviolet radiation transorber are likely to be solids. However, the colorant and/or the transorber can be liquid. It is only necessary for the composition to be a solid.

Because the solid colored composition of the present invention is a solid, the effectiveness of the ultraviolet radiation transorber in effecting the mutation of the colorant is aided if the colorant and the ultraviolet radiation transorber are in intimate contact. To this end, the thorough blending of the two components, along with other components which may be present, is desirable. Such blending generally is accomplished by any of the means known to those having ordinary skill in the art. When the colored composition includes a polymer, blending is facilitated if the colorant and the ultraviolet radiation transorber are at least partly soluble in softened or molten polymer. In such case, the composition is readily prepared in, for example, a two-roll mill.

For some applications, the solid colored composition of the present invention should be utilized in particulate form. In other applications, the particles of the composition should be very small. For example, the particles of a solid colored composition adapted for use as a toner in an electrophotographic process typically consist of 7–15 micrometer average diameter particles, although smaller or larger particles can be employed. Methods of forming such particles are well known to those having ordinary skill in the art.

Photochemical processes involve the absorption or light quanta, or photons, by a molecule, e.g., the ultraviolet radiation transorber, to produce a highly reactive electronically excited state. However, the photon energy, which is proportional to the wavelength of the radiation, cannot be absorbed by the molecule unless it matches the energy difference between the unexcited, or original, state and an excited state. Consequently, while the wavelength range of the ultraviolet radiation to which the solid colored composition is exposed is not directly of concern, at least a portion of the radiation must have wavelengths which will provide the necessary energy to raise the ultraviolet radiation transorber to an energy level which is capable of interacting with the colorant.

It follows, then, that the absorption maximum of the ultraviolet radiation transorber ideally will be matched with the wavelength range of the ultraviolet radiation in order to increase the efficiency of the mutation of the colorant. Such efficiency also will be increased if the wavelength range of the ultraviolet radiation is relatively narrow, with the maximum of the ultraviolet radiation transorber coming within such range. For these reasons, especially suitable ultraviolet radiation has a wavelength of from about 100 to about 375 nanometers. Ultraviolet radiation within this range desirably may be incoherent, pulsed ultraviolet radiation from a dielectric barrier discharge excimer lamp.

The term "incoherent, pulsed ultraviolet radiation" has reference to the radiation produced by a dielectric barrier discharge excimer lamp (referred to hereinafter as "excimer lamp"). Such a lamp is described, for example, by U. Kogelschatz, "Silent discharges for the generation of ultraviolet and vacuum ultraviolet excimer radiation," *Pure & Appl. Chem.*, 62, No. 9, pp. 1667–1674 (1990); and E. Eliasson and U. Kogelschatz, "UV Excimer Radiation from Dielectric-Barrier Discharges," *Appl. Phys. B*, 46, pp. 299–303 (1988). Excimer lamps were developed originally by ABB Infocom Ltd., Lenzburg, Switzerland. The excimer lamp technology since has been acquired by Haräus Noblelight AG, Hanau, Germany.

The excimer lamp emits radiation having a very narrow bandwidth, i.e., radiation in which the half width is of the order of 5–15 nanometers. This emitted radiation is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification. Thus, in comparison with most other commercially useful sources of ultraviolet radiation which typically emit over the entire ultraviolet spectrum and even into the visible region, excimer lamp radiation is essentially monochromatic.

Excimers are unstable molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. Known excimers in general emit in the range of from about 125 to about 360 nanometers, depending upon the excimer gas mixture.

Although the colorant and the ultraviolet radiation transorber have been described as separate compounds, they can be part of the same molecule. For example, they can be covalently coupled to each other, either directly, or indirectly through a relatively small molecule, or spacer. Alternatively, the colorant and ultraviolet radiation transorber can be covalently coupled to a large molecule, such as an oligomer or a polymer, particularly when the solid colored composition of the present invention is adapted to be utilized as a toner in an electrophotographic process. Other variations will be readily apparent to those having ordinary skill in the art.

When the solid colored composition is adapted to be utilized as a toner in an electrophotographic process, the composition also will contain a carrier, the nature of which is well known to those having ordinary skill in the art. For many applications, the carrier will be a polymer, typically a thermosetting or thermoplastic polymer, with the latter being the more common.

Examples of thermoplastic polymers include, by way of illustration only, end-capped polyacetals, such as poly (oxymethylene) or polyformaldehyde, poly (trichloroacetaldehyde), poly(n-valeraldehyde), poly (acetaldehyde), poly(propionaldehyde), and the like; acrylic polymers, such as polyacrylamide, poly(acrylic acid), poly (methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly (chlorotrifluoroethylene), ethylene-chlorotrifluoroethylene copolymers, poly(vinylidene fluoride), poly(vinyl fluoride), and the like; epoxy resins, such as the condensation products of epichlorohydrin and bisphenol A; polyamides, such as poly(6-aminocaproic acid) or poly(ε-caprolactam), poly (hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly (sulfonyl-1,4-phenylene-oxy-1,4-phenylehesulfonyl-4,4'-biphenylene), and the like; polycarbonates, such as poly (bisphenol A) or poly(carbonyldioxy-1,4-phenyleneisopropylidene-1,4-phenylene), and the like; polyesters, such as poly(ethylene terephthalate), poly (tetramethylene terephthalate), poly(cyclohexylene-1,4-dimethylene terephthalate) or poly(oxymethylene-1,4-cyclohexylenemethyleneoxytere-phthaloyl), and the like; polyaryl sulfides, such as poly(p-phenylene sulfide) or poly (thio-1,4-phenylene), and the like; polyimides, such as poly-(pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-l-pentene), 1,2-poly-1,3-butadiene, 1,4-poly-1,3-butadiene, polyisoprene, polychloroprene, polyacrylonitrile, poly(vinyl acetate), poly (vinylidene chloride), polystyrene, and the like; and copolymers of the foregoing, such as acrylonitrile-butadiene-styrene (ABS) copolymers, styrene-n-butylmethacrylate copolymers, ethylene-vinyl acetate copolymers, and the like.

Some of the more commonly used thermoplastic polymers include styrene-n-butyl methacrylate copolymers, polystyrene, styrene-n-butyl acrylate copolymers, styrene-butadiene copolymers, polycarbonates, poly(methyl methacrylate), poly(vinylidene fluoride), polyamides (nylon-12), polyethylene, polypropylene, ethylene-vinyl acetate copolymers, and epoxy resins.

Examples of thermosetting polymers include, again by way of illustration only, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

In addition to the colorant, ultraviolet radiation transorber, and optional carrier, the solid colored composition of the present invention also can contain additional components, depending upon the application for which it is intended. For example, a composition which is to be utilized as a toner in an electrophotographic process also can contain, for example, charge carriers, stabilizers against thermal oxidation, viscoelastic properties modifiers, cross-linking agents, plasticizers, and the like. For some applications, the charge carrier will be the major component of the toner. Charge carriers, of course, are well known to those having ordinary skill in the art and typically are polymer-coated metal particles.

The amount or dosage level of ultraviolet radiation in general will be that amount which is necessary to mutate the colorant. The dosage level, in turn, typically is a function of the time of exposure and the intensity or flux of the radiation source which irradiates the solid colored composition. The latter is effected by the distance of the composition from the source and, depending upon the wavelength range of the ultraviolet radiation, can be effected by the atmosphere between the radiation source and the composition. Accordingly, in some instances it may be appropriate to expose the composition to the radiation in a controlled atmosphere or in a vacuum, although in general neither approach is desired.

The solid colored composition of the present invention can be utilized on or in any substrate. If the composition is present in a substrate, however, the substrate should be substantially transparent to the ultraviolet radiation which is employed to mutate the colorant. That is, the ultraviolet radiation will not significantly interact with or be absorbed by the substrate. As a practical matter, the composition typically will be placed on a substrate, with the most common substrate being paper. Other substrates, such as woven and nonwoven webs or fabrics, films, and the like, can be used, however.

When the solid colored composition is employed as a toner for an electrophotographic process, several variations are possible and come within the scope of the present invention. For example, the composition-based toner can be used to form a first image on a virgin paper sheet. The sheet then can be recycled by exposing the sheet to ultraviolet radiation in accordance with the present invention to render the colorant, and, as a consequence, the composition, colorless. A second image then can be formed on the sheet. The second image can be formed from a standard, known toner, or from a composition-based toner which is either the same as or different from the composition-based toner which was used to form the first image. If a composition-based toner is used to form the second image, the sheet can be recycled again, with the number of cycles being limited by the build-up of now colorless composition on the surface of the paper. However, any subsequent image can be placed on either side of the sheet. That is, it is not required that a second image be formed on the side of the sheet on which the first image was formed.

In addition, the conversion of the composition-based toner image on the sheet to a colorless form does not have to take place on the sheet. For example, sheets having images formed from composition-based toners can be recycled in the traditional way. In place of the usual deinking step, however, the sheets are exposed to ultraviolet radiation, either before or after being converted to pulp. The colorless toner then simple becomes incorporated into the paper formed from the resulting pulp.

The present invention is further described by the examples which follow. Such examples, however, are not to be construed as limiting in any way either the spirit or scope of the present invention. In the examples, all parts are parts by weight unless stated otherwise.

EXAMPLE 1

This example describes the preparation of films consisting of colorant, ultraviolet radiation transorber, and thermoplastic polymer. The colorant and ultraviolet radiation transorber were ground separately in a mortar. The desired amounts of the ground components were weighed and placed in an aluminum pan, along with a weighed amount of a thermoplastic polymer. The pan was placed on a hot plate set at 150° C. and the mixture in the pan was stirred until molten. A few drops of the molten mixture were poured onto a steel plate and spread into a thin film by means of a glass microscope slide. Each steel plate was 3×5 inches (7.6 cm×12.7 cm) and was obtained from Q-Panel Company, Cleveland, Ohio. The film on the steel plate was estimated to have a thickness of the order of 10–20 micrometers.

In every instance, the colorant was Malachite Green oxalate (Aldrich Chemical Company, Inc., Milwaukee, Wis.), referred to hereinafter as Colorant A for convenience. The ultraviolet radiation transorber (UVRT) consisted of one or more of Irgacure®500(UVRT A), Irgacure®651(UVRT B), and Irgacure®907(UVRT C), each of which was described earlier and is available from Ciba-Geigy Corporation, Hawthorne, N.Y. The polymer was one of the following: an epichlorohydrin-bisphenol A epoxy resin (Polymer A), Epon® 1004F (Shell Oil Company, Houston, Tex.); a poly(ethylene glycol) having a weight-average molecular weight of about 8,000 (Polymer B), Carbowax 8000 (Aldrich Chemical Company); and a poly-(ethylene glycol) having a weight-average molecular weight of about 4,600 (Polymer C), Cirbowax 4600 (Aldrich Chemical Company). A control film was prepared which consisted only of colorant and polymer. The compositions of the films are summarized in Table 1-1.

TABLE 1-1

Compositions of Films Containing
Colorant and Ultraviolet Radiation Transorber (UVRT)

| Film | Colorant Type | Colorant Parts | UVRT Type | UVRT Parts | Polymer Type | Polymer Parts |
|------|------|-------|------|-------|------|-------|
| A | A | 1 | A | 6 | A | 90 |
|   |   |   | C | 4 |   |   |
| B | A | 1 | A | 12 | A | 90 |
|   |   |   | C | 8 |   |   |
| C | A | 1 | A | 18 | A | 90 |
|   |   |   | C | 12 |   |   |
| D | A | 1 | A | 6 | A | 90 |
|   |   |   | B | 4 |   |   |
| E | A | 1 | B | 30 | A | 70 |
| F | A | 1 | — | — | A | 100 |
| G | A | 1 | A | 6 | B | 90 |
|   |   |   | C | 4 |   |   |
| H | A | 1 | B | 10 | C | 90 |

While still on the steel plate, each film was exposed to ultraviolet radiation. In each case, the steel plate having the film sample on its surface was placed on a moving conveyor belt having a variable speed control. Three different ultraviolet radiation sources, or lamps, were used. Lamp A was a 222-nanometer excimer lamp and Lamp B was a 308-nanometer excimer lamp, as already described. Lamp C was a fusion lamp system having a "D" bulb (Fusion Systems Corporation, Rockville, Md.). The excimer lamps were organized in banks of four cylindrical lamps having a length of about 30 cm, with the lamps being oriented normal to the direction of motion of the belt. The lamps were cooled by circulating water through a centrally located or inner tube of the lamp and, as a consequence, they operated at a relatively low temperature, i.e., about 50° C. The power density at the lamp's outer surface typically is in the range of from about 4 to about 20 joules per square meter ($J/m^2$). However, such range in reality merely reflects the capabilities of current excimer lamp power supplies; in the future, higher power densities may be practical. With Lamps A and B, the distance from the lamp to the film sample was 4.5 cm and the belt was set to move at 20 ft/min (0.1 m/sec). With Lamp C, the belt speed was 14 ft/min (0.07 m/sec) and the lamp-to-sample distance was 10 cm. The results of exposing the film samples to ultraviolet radiation are summarized in Table 1-2. Except for Film F, the table records the number of passes under a lamp which were required in order to render the film colorless. For Film F, the table records the number of passes tried, with the film in each case remaining colored (no change).

TABLE 1-2

Results of Exposing Films Containing
Colorant and Ultraviolet Radiation Transorber (UVRT)
to Ultraviolet Radiation

| Film | Excimer Lamp — Lamp A | Excimer Lamp — Lamp B | Fusion Lamp |
|------|-------|-------|-------|
| A | 3 | 3 | 15 |
| B | 2 | 3 | 10 |
| C | 1 | 3 | 10 |
| D | 1 | 1 | 10 |
| E | 1 | 1 | 1 |
| F | 5 | 5 | 10 |
| G | 3 | — | 10 |
| H | 3 | — | 10 |

EXAMPLE 2

This example describes the preparation of solid colored compositions adapted to be utilized as toners in an electrophotographic process. In every instance, the toner included Colorant A as described in Example 1; a polymer, DER 667, an epichlorohydrin-bisphenol A epoxy resin (Polymer D), Epon® 1004F (Dow Chemical Company, Midland, Mich.); and a charge carrier, Carrier A, which consisted of a very finely divided polymer-coated metal. The ultraviolet radiation transorber (UVRT) consisted of one or more of UVRT B from Example 1, Irgacure® 369 (UVRT D), and Irgacure® 184 (UVRT E); the latter two transorbers were described earlier and are available from Ciba-Geigy Corporation, Hawthorne, N.Y. In one case, a second polymer also was present, styrene acrylate 1221, a styrene-acrylic acid copolymer (Hercules Incorporated, Wilmington, Del.).

To prepare the toner, colorant, ultraviolet radiation transorber, and polymer were melt-blended in a Model 3VV 800E, 3 inch×7 inch (7.6 cm ×17.8 cm) two-roll research mill (Farrel Corporation, Ansonia, Conn.). The resulting melt-blend was powdered in a Mikropul hammermill with a 0.010-inch herringbone screen (R. D. Kleinfeldt, Cincinnati, Ohio) and then sieved for proper particle sizes in a Sturtvant, air two-inch micronizer (R. D. Kleinfeldt) to give what is referred to herein as a pretoner. Charge carrier then was added to the pretoner and the resulting mixture blended thoroughly. Table 2-1 summarizes the compositions of the pretoners and Table 2-2 summarizes the compositions of the toners.

TABLE 2-1

Summary of Pretoner Compositions

| Pretoner | Colorant A (g) | UVRT Type | UVRT g | Polymer Type | Polymer g |
|------|------|------|------|------|------|
| A | 1 | D | 20 | D | 80 |
| B | 1 | B | 20 | D | 80 |
| C | 1 | B | 10 | D | 80 |
|   |   | D | 10 |   |   |
| D | 1 | B | 6.9 | D | 40 |
|   |   | D | 6.6 | E | 40 |
|   |   | E | 6.6 |   |   |

TABLE 2-2

Summary of Toner Compositions

| Toner | Pretoner Type | Pretoner g | Charge Carrier (g) |
|------|------|------|------|
| A | A | 8.4 | 210 |
| B | B | 8.4 | 210 |
| C | C | 8.4 | 210 |
| D | D | 8.4 | 210 |

Each toner was placed separately in a Sharp Model ZT-50TD1 toner cartridge and installed in either a Sharp Model Z-76 or a Sharp Model Z-77 xerographic copier (Sharp Electronics Corporation, Mahwah, N.J.). Images were made in the usual manner on bond paper (Neenah Bond). The image-bearing sheets then were exposed to ultraviolet radiation from Lamp B as described in Example 1. In each case, the image was rendered colorless with one pass.

Having thus described the invention, numerous changes and modifications hereof will be readily apparent to those having ordinary skill in the art without departing from the spirit or scope of the invention.

What is claimed is:

1. An electrophotographic process comprising the steps of:

creating an image on a photoreceptor surface;

applying a toner to the photoreceptor surface to form a toner image which replicates the image, the toner comprising a mutable colorant, an ultraviolet radiation transorber, and a carrier comprising a polymer;

transferring the toner image to a substrate; and fixing the toner image to the substrate, wherein the ultraviolet radiation transorber is adapted, upon exposure to ultraviolet radiation, to interact with the mutable colorant to irreversibly mutate the mutable colorant from an initial absorption maximum to a new absorption maximum different from the initial absorption maximum.

2. The electrophotographic process of claim 1, wherein the toner further comprises a charge carrier.

3. The electrophotographic process of claim 1, wherein the ultraviolet radiation transorber absorbs ultraviolet light at a wavelength of from about 100 to about 375 nanometers.

4. The electrophotographic process of claim 3, wherein the ultraviolet radiation is incoherent, pulsed ultraviolet radiation from a dielectric barrier discharge excimer lamp.

5. The electrophotographic process of claim 1, wherein the mutable colorant and the ultraviolet radiation transorber are in intimate contact.

6. The electrophotographic process of claim 1 wherein the mutable colorant is selected from the group consisting of triaryl methyl dyes, monoazo dyes, thiazine dyes, oxazine dyes, naphthalimide dyes, azine dyes, cyanine dyes, indigo dyes, coumarin dyes, benzimidazole dyes, paraquinoidal dyes, fluorescein dyes, diazonium salt dyes, azoic diazo dyes, phenylenediamine dyes, disazo dyes, antiraquinone dyes, trisazo dyes, xanthene dyes, proflavine dyes, sulfonephthalein dyes, phthalocyanine dyes, carotenoid dyes, carminic acid dyes, azure dyes, and acridine dyes.

7. The electrophotographic process of claim 6 wherein the ultraviolet light transorber is selected from the group consisting of benzildimethyl ketal, 1-hydroxycyclohexyl phenyl ketone, 2-methyl-1 -[4-(methylthio)phenyl]-2-morpholino-propan-1-one], 2-benzyl-2-dimethylamino-1-(4-morpholinophenyl)butan-1-one, 1-hydroxycyclohexyl phenyl ketone, p-dimethylaminophenyl ketone), trimethyl stannate, bis[4-(diphenyl-sulphonio)phenyl)] sulfide bis (hexafluorophosphate), ($n^5$-2,4-(cyclopentadien-1-yl)[(1,2,3,4,5,6-n)-(1-methylethyl)benzene]iron(1+) hexafluorophosphate.

8. The electrophotographic process of claim 1 wherein the ultraviolet light transorber is selected from the group consisting of benzildimethyl ketal, 1-hydroxycyclohexyl phenyl ketone, 2-methyl-1-[4-(methylthio)phenyl]-2-morpholino-propan-1-one], 2-benzyl-2-dimethylamino-1-(4-morpholinophenyl)butan-1-one, 1-hydroxycyclohexyl phenyl ketone, p-dimethylaminophenyl ketone), trimethyl stannate, bis[4-(diphenyl-sulphonio)phenyl)] sulfide bis (hexafluorophosphate), ($n^5$-2,4-(cyclopentadien-1yl)[(1,2,3,4,5,6-n)-(1-methylethyl)benzene]iron(1+) hexafluorophosphate.

9. An electrophotographic process comprising the steps of:

providing a substrate having a first image thereon which is formed by a first toner which comprises: a mutable colorant; an ultraviolet radiation transorber; and a carrier for the colorant and the ultraviolet radiation transorber; wherein the carrier comprises a polymer, and the ultraviolet radiation transorber is adapted, upon exposure to ultraviolet radiation, to interact with the mutable colorant to irreversibly mutate the mutable colorant from an initial absorption maximum to a new absorption maximum which is different from the initial absorption maximum;

exposing the first image on the substrate to ultraviolet radiation at a dosage level sufficient to irreversibly mutate the colorant;

creating a second image on a photoreceptor surface;

applying a second toner to the photoreceptor surface to form a toner image which replicates the second image;

transferring the second toner image to the substrate; and fixing the second toner image to the substrate.

10. The electrophotographic process of claim 9, wherein the first toner further comprises a charge carrier.

11. The electrophotographic process of claim 9, wherein the mutable colorant and the ultraviolet radiation transorber are in intimate contact.

12. The electrophotographic process of claim 9, wherein the ultraviolet radiation transorber absorbs ultraviolet radiation at a wavelength of from about 100 to about 375 nanometers.

13. The electrophotographic process of claim 12, wherein the ultraviolet radiation is incoherent, pulsed ultraviolet radiation from a dielectric barrier discharge excimer lamp.

14. The electrophotographic process of claim 9, in which the second toner comprises:

a second mutable colorant;

a second ultraviolet radiation transorber; and a second carrier for the second colorant and the second ultraviolet radiation transorber, and wherein the second carrier comprises a polymer, and the second ultraviolet radiation transorber is adapted, upon exposure to ultraviolet radiation, to interact with the second mutable colorant to irreversibly mutate the second mutable colorant from an initial absorption maximum to a new absorption maximum different from the initial absorption maximum.

15. The electrophotographic process of claim 14, wherein the second toner includes a charge carrier.

16. The electrophotographic process of claim 14, wherein the second mutable colorant and the second ultraviolet radiation transorber are in intimate contact.

17. The electrophotographic process of claim 14, wherein the ultraviolet radiation has a wavelength of from about 100 to about 375 nanometers.

18. The electrophotographic process of claim 17, wherein the ultraviolet radiation transorber absorbs ultraviolet radiation at a wavelength of from about 100 to about 375 nanometers.

19. The electrophotographic process of claim 9 wherein the mutable colorant is selected from the group consisting of triaryl methyl dyes, monoazo dyes, thiazine dyes, oxazine dyes, naphthalimide dyes, azine dyes, cyanine dyes, indigo dyes, courmarin dyes, benzimidazole dyes, paraquinoidal dyes, fluorescein dyes, diazonium salt dyes, azoic diazo dyes, phenylenediamine dyes, disazo dyes, anthraquinone dyes, trisazo dyes, xanthene dyes, proflavine dyes, sulfonephthalein dyes, phthalocyanine dyes, carotenoid dyes, carminic acid dyes, azure dyes, and acridine dyes.

20. The electrophotographic process of claim 9 wherein the ultraviolet light transorber is selected from the group consisting of benzildimethyl ketal, 1-hydroxycyclohexyl phenyl ketone, 2-methyl-1-[4-(methylthio)phenyl]-2- morpholino-propan-1-one], 2-2-dimethylamino-1-(4-morpholinophenyl)butan-1-one, 1-hydroxycyclohexyl phenyl ketone, p-dimethylaminophenyl ketone), trimethyl stannate, bis[4-(diphenyl-sulphonio)phenyl)] sulfide bis(hexafluorophosphate), ($n^5$-2,4-(cyclopentadien-1-yl)[(1,2,3,4,5,6-n-(methylethyl)benzene]-iron(1+) hexafluorophosphate.

21. The electrophotographic process of claim 20 wherein the ultraviolet light transorber is selected from the group consisting of benzildimethyl ketal, 1-hydroxycyclohexyl phenyl ketone, 2- methyl-1-[4-(methylthio)phenyl]-2-morpholino-propan-1-one], 2-benzyl-2-dimethylamino-1-(4-morpholinophenyl)butan-1-one, 1-hydroxycyclohexyl 2-dimethylamino-1-(4-morpholinophenyl)butan-1-one, 1-hydroxycyclophenyl ketone, p-dimethylaminophenyl ketone), trimethyl s bis[4-(diphenyl-sulphonio)phenyl)] sulfide bis(hexafluorophosphate), ($n^5$-2,4-(cyclopentadien-1-yl)[(1,2,3,4,5,6-n-(methylethyl)benzene]-iron(1+) hexafluorophosphate.

22. An electrophotographic process comprising the step of applying a toner to a photoreceptor surface to form a toner image which replicates a first image, the toner comprising a mutable colorant, an ultraviolet radiation transorber, and a carrier comprising a polymer; wherein the ultraviolet radiation transorber is adapted, upon exposure to ultraviolet radiation, to interact with the mutable colorant to irreversibly mutate the mutable colorant from an initial absorption maximum to a new, absorption maximum different from the initial absorption maximum.

23. An electrophotographic process comprising the steps of:

providing a substrate having a first image thereon which is formed by a first toner which comprises: a mutable colorant; an ultraviolet radiation transorber in intimate contact with the ultraviolet radiation transorber; and a carrier for the colorant and the ultraviolet radiation transorber; wherein the carrier comprises a polymer, and the ultraviolet radiation transorber is adapted, upon exposure to incoherent, pulsed ultraviolet radiation from a dielectric barrier discharge excimer lamp and having a wavelength of from about 125 to about 360 nanometers, to interact with the mutable colorant to irreversibly mutate the mutable colorant from an initial absorption maximum to a new absorption maximum which is different from the initial absorption maximum;

exposing the first image on the substrate to incoherent, pulsed ultraviolet radiation from a dielectric barrier discharge excimer lamp at a wavelength of from about 125 to about 360 nanometers and a dosage level sufficient to irreversibly mutate the colorant;

creating a second image on a photoreceptor surface;

applying a second toner to the photoreceptor surface to form a toner image which replicates the second image;

transferring the second toner image to the substrate; and fixing the second toner image to the substrate.

* * * * *